US011062805B2

(12) United States Patent
Binninger et al.

(10) Patent No.: US 11,062,805 B2
(45) Date of Patent: Jul. 13, 2021

(54) CELL PROCESSING SYSTEM AND METHOD WITH PROCESS PARAMETER CONTROL

(71) Applicant: Fenwal, Inc., Lake Zurich, IL (US)

(72) Inventors: Steven Binninger, Frankfurt am Main (DE); Christopher J. Wegener, Libertyville, IL (US); Alaina Schlinker, Chicago, IL (US); Bret M. Olson, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 17/080,777

(22) Filed: Oct. 26, 2020

(65) Prior Publication Data

US 2021/0043317 A1 Feb. 11, 2021

Related U.S. Application Data

(63) Continuation of application No. 15/456,804, filed on Mar. 13, 2017.
(Continued)

(51) Int. Cl.
*G16H 40/63* (2018.01)
*G05B 13/02* (2006.01)
(Continued)

(52) U.S. Cl.
CPC ............ *G16H 40/63* (2018.01); *A61M 1/265* (2014.02); *A61M 1/3692* (2014.02);
(Continued)

(58) Field of Classification Search
None
See application file for complete search history.

(56) References Cited

U.S. PATENT DOCUMENTS

| 3,877,634 A | 4/1975 | Rohde et al. |
| 4,835,372 A | 5/1989 | Gombrich et al. |

(Continued)

FOREIGN PATENT DOCUMENTS

| DE | 20305506 | 1/2004 |
| EP | 3188062 | 7/2007 |

(Continued)

OTHER PUBLICATIONS

Fresenius Kabi, Lovo Cell processing system, Filtration Technology Designed for Labs Like Yours (2014).
(Continued)

*Primary Examiner* — Bernard G Lindsay
(74) *Attorney, Agent, or Firm* — Becker Patent Law, LLC

(57) ABSTRACT

A cell washing system includes a fluid circuit, a source container, a source of wash solution, a pump, and a separator device. The system also includes a touch screen configured to receive user input and to display data to a user, and a controller coupled to the touch screen and configured to control the separator device and pump to operate a wash procedure, wherein the controller is configured to receive from the touch screen user input data for at least one protocol, the at least one protocol including values for a set of process parameters for a wash procedure, to store the at least one protocol in a memory, to receive an identifier associated with a user, to apply the at least one protocol based at least in part on the identifier, and to operate the wash procedure using the applied protocol.

19 Claims, 5 Drawing Sheets

Related U.S. Application Data

(60) Provisional application No. 62/308,015, filed on Mar. 14, 2016.

(51) Int. Cl.

| | | |
|---|---|---|
| *A61M 1/36* | (2006.01) | |
| *A61M 1/26* | (2006.01) | |
| *G16H 40/67* | (2018.01) | |
| *G16H 10/40* | (2018.01) | |
| *G16H 20/17* | (2018.01) | |

(52) U.S. Cl.
CPC ........... *G05B 13/024* (2013.01); *G16H 10/40* (2018.01); *G16H 40/67* (2018.01); *A61M 2205/50* (2013.01); *A61M 2205/502* (2013.01); *A61M 2205/60* (2013.01); *G16H 20/17* (2018.01)

(56) References Cited

U.S. PATENT DOCUMENTS

| | | |
|---|---|---|
| 5,053,121 A | 10/1991 | Schoendorfer et al. |
| 5,194,145 A | 3/1993 | Schoendorfer |
| 5,240,856 A | 8/1993 | Goffe et al. |
| 5,458,566 A | 10/1995 | Herrig et al. |
| 5,478,479 A * | 12/1995 | Herrig .................... A61M 1/02 210/745 |
| 5,536,475 A | 7/1996 | Moubayed et al. |
| 5,573,678 A | 11/1996 | Brown et al. |
| 5,769,811 A | 6/1998 | Stacey et al. |
| 5,865,718 A | 2/1999 | Chan |
| 5,956,023 A | 9/1999 | Lyle et al. |
| 6,060,022 A | 5/2000 | Pang et al. |
| 6,175,420 B1 | 1/2001 | Barry et al. |
| 6,284,142 B1 | 9/2001 | Muller |
| 6,325,775 B1 | 12/2001 | Thom et al. |
| 6,466,879 B1 | 10/2002 | Cantu et al. |
| 6,605,223 B2 | 8/2003 | Jorgensen et al. |
| 6,622,052 B1 | 9/2003 | Rosiello |
| 6,716,151 B2 | 4/2004 | Panzani et al. |
| 6,730,054 B2 | 5/2004 | Pierce et al. |
| 6,736,788 B1 | 5/2004 | Mongomery et al. |
| 7,044,927 B2 | 5/2006 | Mueller et al. |
| 7,072,769 B2 | 7/2006 | Fletcher-Haynes et al. |
| 7,363,167 B2 | 4/2008 | Csore et al. |
| 7,390,484 B2 | 6/2008 | Fraser et al. |
| 7,430,478 B2 | 9/2008 | Fletcher-Haynes et al. |
| 7,651,474 B2 | 1/2010 | Van Waeg et al. |
| 7,963,901 B2 | 6/2011 | Langley et al. |
| 8,150,548 B2 | 4/2012 | Raghibizadeh et al. |
| 8,357,298 B2 | 1/2013 | Demers et al. |
| 8,415,145 B2 | 4/2013 | Fukuda et al. |
| 8,539,573 B2 | 9/2013 | Newlin et al. |
| 8,883,499 B2 | 11/2014 | Hedrick et al. |
| 8,900,172 B2 | 12/2014 | Pohlmeier |
| 8,905,959 B2 | 12/2014 | Basaglia |
| 8,945,376 B1 | 2/2015 | Cordisco |
| 2002/0179544 A1* | 12/2002 | Johnson ............... A61M 1/3403 210/806 |
| 2003/0018289 A1 | 1/2003 | Ng et al. |
| 2003/0069480 A1 | 4/2003 | Ng et al. |
| 2003/0093503 A1 | 5/2003 | Yamaki et al. |
| 2003/0199379 A1 | 10/2003 | Schneider et al. |
| 2003/0208621 A1 | 11/2003 | Bowman |
| 2004/0248077 A1 | 12/2004 | Rodriguez Rilo et al. |
| 2005/0070837 A1 | 3/2005 | Ferrarini et al. |
| 2005/0215937 A1 | 9/2005 | Spinale et al. |
| 2005/0234381 A1 | 10/2005 | Niemetz et al. |
| 2007/0219826 A1 | 9/2007 | Brodsky et al. |
| 2007/0250832 A1 | 10/2007 | Rahn et al. |
| 2008/0040153 A1 | 2/2008 | Davis, Jr. |
| 2008/0124700 A1* | 5/2008 | Fortini .................... B04B 11/02 435/2 |
| 2008/0249386 A1* | 10/2008 | Besterman ............ A61B 5/0022 600/365 |
| 2009/0191174 A1 | 7/2009 | Boudreau et al. |
| 2010/0313105 A1 | 12/2010 | Nekoomaram et al. |
| 2011/0045959 A1 | 2/2011 | Kurihara et al. |
| 2011/0078246 A1 | 3/2011 | Ditmer-Roche et al. |
| 2011/0206643 A1 | 8/2011 | Fulga et al. |
| 2011/0209212 A1* | 8/2011 | Newlin .................... G05B 1/00 726/17 |
| 2011/0244443 A1 | 10/2011 | van Rijn et al. |
| 2012/0116347 A1 | 5/2012 | Weinert et al. |
| 2013/0092630 A1 | 4/2013 | Wegener |
| 2013/0102963 A1 | 4/2013 | Marsh et al. |
| 2013/0267884 A1 | 10/2013 | Boggs et al. |
| 2013/0299399 A1 | 11/2013 | Suffritti et al. |
| 2013/0310726 A1 | 11/2013 | Miller et al. |
| 2013/0317850 A1 | 11/2013 | Bene et al. |
| 2013/0334139 A1 | 12/2013 | Blickhan et al. |
| 2014/0081193 A1 | 3/2014 | Watters et al. |
| 2014/0194817 A1* | 7/2014 | Lee .................... A61M 5/14228 604/151 |
| 2014/0234183 A1 | 8/2014 | Kolenbrander et al. |
| 2014/0266983 A1 | 9/2014 | Christensen |
| 2014/0282181 A1 | 9/2014 | Declerck |
| 2016/0124009 A1 | 5/2016 | Wasson et al. |
| 2016/0300028 A1 | 10/2016 | Abell |
| 2017/0340783 A1 | 11/2017 | Wegener et al. |
| 2018/0015418 A1 | 1/2018 | Binninger et al. |
| 2018/0240322 A1 | 8/2018 | Potucck et al. |

FOREIGN PATENT DOCUMENTS

| | | |
|---|---|---|
| EP | 2745864 | 6/2014 |
| JP | 2006-167345 | 6/2006 |
| WO | WO81/02979 | 10/1981 |
| WO | WO00/20053 | 4/2000 |
| WO | WO02/062484 | 8/2002 |
| WO | WO02/069793 | 9/2002 |
| WO | WO02/088897 | 11/2002 |
| WO | WO02/089340 | 11/2002 |
| WO | WO2004/032999 | 4/2004 |
| WO | WO2009/072510 | 6/2009 |
| WO | WO2012/021167 | 2/2012 |
| WO | WO2012/125457 | 9/2012 |
| WO | WO2012/125470 | 9/2012 |
| WO | WO2013/025394 | 2/2013 |

OTHER PUBLICATIONS

Fresenius Kabi, Lovo Cell Processing System, Choose filtered (2014).
European Patent Office, European Search Report and Search Opinion, counterpart EP Appl. No. 17160555, dated Jul. 25, 2017.
European Patent Office, Communication, counterpart EP Appl. No. 17160555, dated Mar. 11, 2019.
CaridianBCT, Trima Accel® Automated Blood Collection System Operator's Manual (Jun. 2010) (296 pages).
Fresenius Kabi, LOVO Cell Processing System Operator's Manual (Jun. 2014) (124 pages).
Fresenius Kabi, LOVO Cell Processing System Administrator's Guide (Jun. 2014) (32 pages).
Letter dated Sep. 11, 2019 in EPA 17160555.3, 4 pages.
Summons for Oral Proceedings dated May 19, 2020 in 18 pages.
Letter dated Sep. 18, 2020 in EPA 17160555.3 and claims, 11 pages.
Consultation by telephone with the applicant dated Oct. 7, 2020 in EPA1760555.3, 1 page.
Decision of the Examining Division dated Mar. 15, 2021 in EPA176055, 19 pages.
Cell Saver Elite, Autologous Blood Recovery System, (c)2016 Haemonetics Corp, 8 pages.

* cited by examiner

CELL PROCESSING SYSTEM AND METHOD WITH PROCESS PARAMETER CONTROL

CROSS-REFERENCE TO RELATED APPLICATIONS

This application is a continuation of U.S. application Ser. No. 15/456,804, filed Mar. 13, 2017, which claims the benefit of U.S. Provisional Application No. 62/308,015, filed Mar. 14, 2016, both of which are hereby incorporated herein by reference.

TECHNICAL FIELD

The present disclosure is generally directed to systems and methods for controlling modifiable process parameters, and to biological fluid processing systems and methods employing such. More particularly, the present disclosure is directed to the controlled processing of biological fluid using a disposable fluid circuit and a reusable processing machine. The present disclosure is also directed to systems and methods for permitting control of the processing based on a hierarchy of authorizations.

BACKGROUND

The processing of biological fluid such as blood or blood components typically involves using a reusable processing machine ("hardware") and a disposable fluid circuit adapted for mounting or other association with the reusable apparatus. The fluid circuit typically includes (plastic) bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

The reusable processing machine is designed so that many different processes may be carried out on a single machine. These processes may vary in accordance with the nature of the fluid circuit used, but even a single fluid circuit may permit a large number of different processes to be performed on biological fluids disposed therein in conjunction with the processing machine. To maintain maximum flexibility and thereby accommodate the widest variety of processes, the machine is conventionally designed to permit its operation to be varied in literally hundreds of different ways.

SUMMARY

In one aspect, a cell washing system includes a fluid circuit, a source container configured to hold a biological cell suspension, the source container including an access site configured to provide access between the source container and the fluid circuit, a source of wash solution configured to hold a wash solution, the source of wash solution including an access site configured to provide access between the source of wash solution and the fluid circuit, wherein the fluid circuit is configured to combine the biological cell suspension and the wash solution, a pump configured to pump the combination of biological cell suspension and wash solution through the fluid circuit, and a separator device including a drive unit and a port, the port configured to receive the combination of biological cell suspension and wash solution, wherein the separator device is configured to separate red blood cells from a waste solution including free hemoglobin, the separator device to dispense the waste solution to a waste product container. The system also includes a touch screen configured to receive user input and to display data to a user, and a controller coupled to the touch screen and configured to control the separator device and pump to operate a wash procedure, wherein the controller is configured to receive from the touch screen user input data for a plurality of protocols, each protocol including values for a set of process parameters for wash procedures, wherein the controller is configured to store each protocol in a memory, wherein the controller is configured to receive an identifier associated with a user, to apply one of the protocols based at least in part on the identifier, and to operate the wash procedure using the applied protocol.

In another aspect, a cell washing system includes a fluid circuit, a source container configured to hold a biological cell suspension, the source container including an access site configured to provide access between the source container and the fluid circuit, a source of wash solution configured to hold a wash solution, the source of wash solution including an access site configured to provide access between the source of wash solution and the fluid circuit, wherein the fluid circuit is configured to combine the biological cell suspension and the wash solution, a pump configured to pump the combination of biological cell suspension and wash solution through the fluid circuit, and a separator device including a drive unit and a port, the port configured to receive the combination of biological cell suspension and wash solution, wherein the separator device is configured to separate red blood cells from a waste solution including free hemoglobin, the separator device to dispense the waste solution to a waste product container. The system also includes a touch screen configured to receive user input and to display data to a user, and a controller coupled to the touch screen and configured to control the separator device and pump to operate a wash procedure, wherein the controller is configured to receive from the touch screen user input data for a protocol, the protocol including values for a set of process parameters for the wash procedure, wherein the controller is configured to receive a numeric value between a minimum value and a maximum value for one of the process parameters of the protocol, wherein the controller is configured to store the protocol having the numeric value in a memory, wherein the controller is configured to receive an identifier associated with a user via the touch screen, to apply the stored protocol based at least in part on the identifier, and to process the biological cell suspension employing the wash procedure having the numeric value.

Other aspects include a cell washing system including a fluid circuit, a source container configured to hold a biological fluid including red blood cells, the source container configured to couple to the fluid circuit, a source of wash solution configured to hold a wash solution, the source of wash solution configured to couple to the fluid circuit, wherein the fluid circuit is configured to combine the biological fluid and the wash solution, a pump configured to pump the combination of biological fluid and wash solution through the fluid circuit, and a separator device including a drive unit and a port, the port configured to receive the combination of biological fluid and wash solution, wherein the separator device is configured to separate the red blood cells from a waste solution including free hemoglobin, the separator device to dispense the waste solution to a waste product container. The system also includes a touch screen configured to receive user input and to display data to a user, and a controller coupled to the touch screen and configured to control the separator device and pump to operate a wash procedure, wherein the controller is configured to receive from the touch screen user input data for a protocol, the protocol including values for a set of process parameters for the wash procedure, wherein the controller is configured to receive a numeric value defining a volume to wash for one of the values, wherein the controller is configured to store the protocol having the numeric value in a memory, wherein the controller is configured to receive a password associated with a user via the touch screen, to determine if the password is associated with an authorization that permits the user to modify the protocol, to receive a modification of the protocol from the user based on the determination, wherein the modification includes a modification of the volume to wash, and to process the biological fluid employing a wash procedure having the modified protocol.

BRIEF DESCRIPTION OF THE FIGURES

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION

Figure 1:
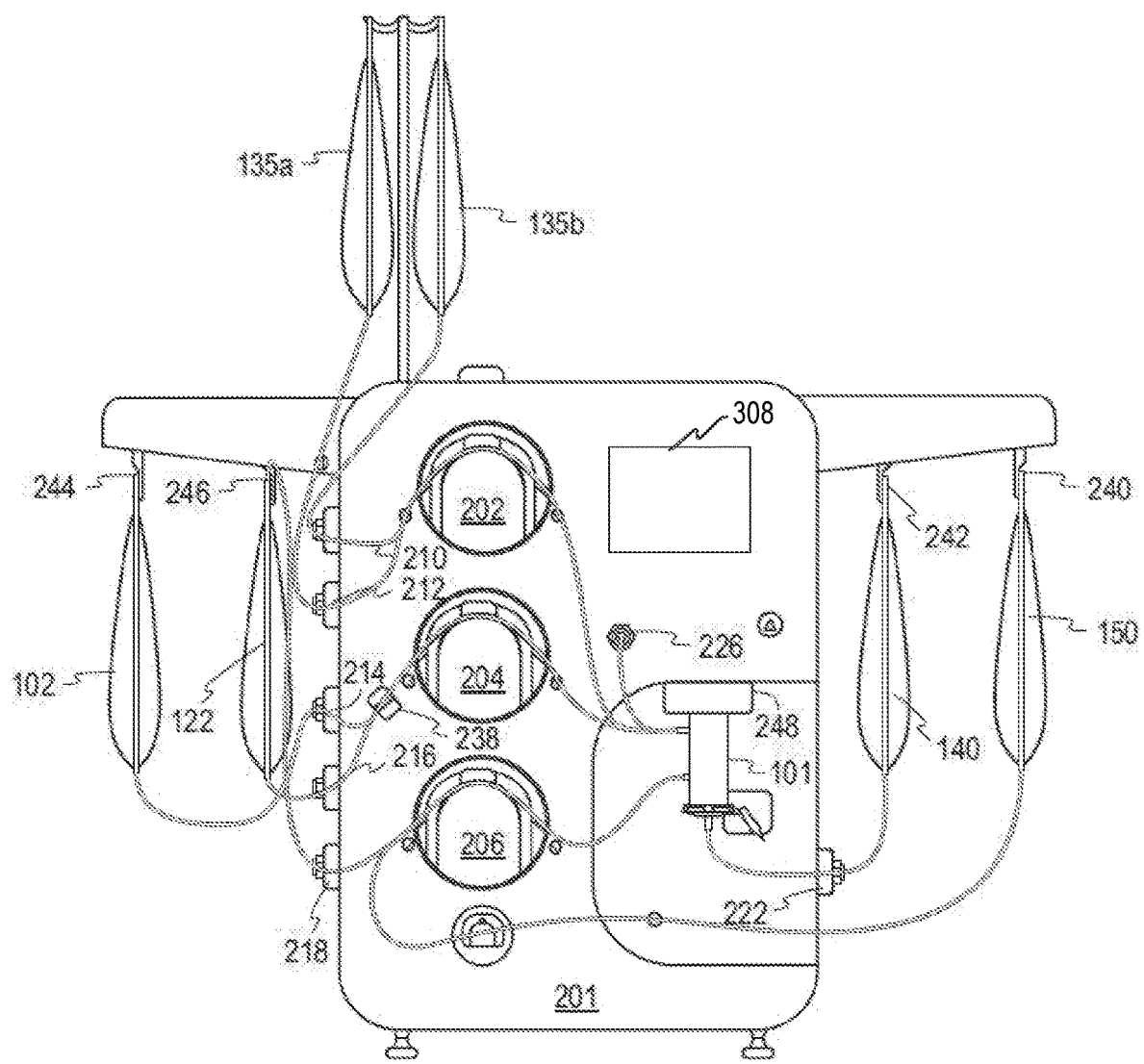
FIG. 1 is a frontal view of a reusable cell processing apparatus with a disposable fluid circuit loaded thereon.
Figure 2:
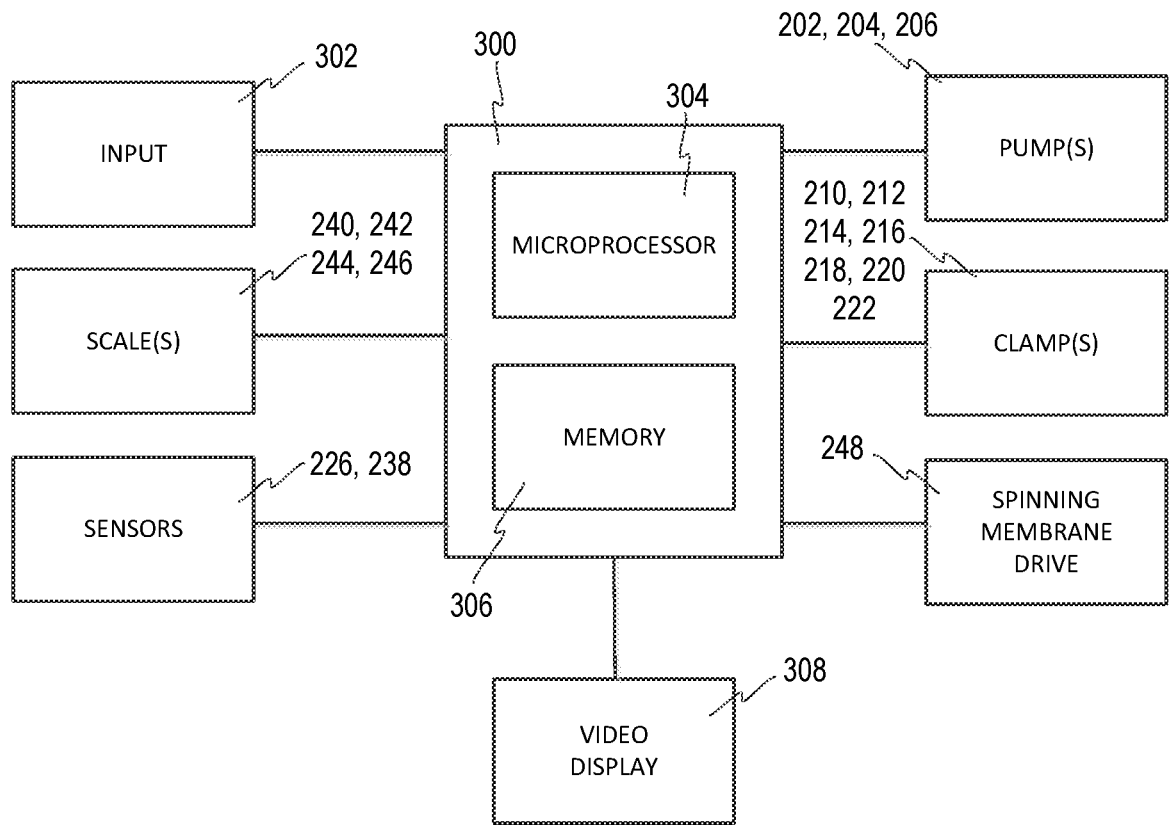
FIG. 2 is a schematic view of the control circuitry of the apparatus of FIG. 1.

As illustrated in FIGS. 1 and 2, a cell processing system includes a processor 100, 200 to receive a biological fluid to be processed, a control unit (or controller) 300 coupled to the processor, the controller 300 configured to operate the processor 100, 200 according to at least one modifiable process parameter, and at least one input 302 coupled to the controller 300, the at least one input 302 configured to receive an identifier and at least one process parameter control associated with the at least one process parameter that limits modification of the at least one process parameter if applied. The controller 300 is configured to determine if the identifier is associated with an administrator authorization and to apply the at least one process parameter control to the at least one process parameter if the identifier is associated with an administrator authorization.

As explained in detail below, the processor 100, 200 includes a disposable fluid circuit 100 (see also FIGS. 3 and 5) and reusable hardware 200 (see also FIG. 4). According to the illustrated embodiments, the disposable fluid circuit 100 may include a spinning membrane 101, at least one container 102, 122, 135a, 135b, 140, 150, and tubing 106, 120, 128, 132a, 132b, 162, 166, 168 connecting the spinning membrane 101 and the one or more containers 102, 122, 135a, 135b, 140, 150, As is also illustrated, the reusable hardware 200 may include at least one drive 248 to spin the spinning membrane 101, at least one scale 240, 242, 244, 246 to weigh the at least one container 102, 122, 140, 150 and contents thereof, and at least one pump 202, 204, 206 to receive the tubing 162, 166, 168 and pump fluid therethrough such as by peristaltic action, although other types of pumps and pumping action may be used.

The controller 300 may, according to the embodiments, include a programmable microprocessor 304, which microprocessor 304 may be coupled to the at least one input 302 and may be programmed to determine if the identifier is associated with an administrator authorization and to apply the processor parameter control to the at least one process parameter if the identifier is associated with an administrator authorization. The identifier, for example in the form of a password, is received from a user via an input, such as a touchscreen, keyboard, keypad or scanner/reader, and is used to determine if the user has authorization to enter the process parameter control. Given the range of identifiers possible, the at least one input may include a first input for entry of the identifier and a second input for entry of the process parameter control. For example, the process parameter control prevents persons lacking proper authorization from changing the process parameter and/or modifying the process parameter beyond a certain range of process parameter values.

In addition, the embodiments illustrate a method of operating a cell processing system, the cell processing system including a processor 100, 200 to receive a biological fluid to be processed and to be operated according to at least one modifiable process parameter. The method includes receiving an identifier and at least one process parameter control associated with the at least one process parameter that limits modification of the at least one process parameter if applied, determining if the identifier is associated with an administrator authorization, applying the at least one processor control to the at least one process parameter if the identifier is associated with an administrator authorization, and processing the biological fluid employing a process that includes the at least one process parameter.

Consequently, an embodiment of the afore-mentioned system and method may provide one or more of the following advantages. First, the system and method may permit a versatile, highly-adaptable cell processing system to provide reproducible results with lessened concern that individual users will modify the processes carried out on the cell processing system in unexpected or, at least, unknown ways. Furthermore, the system and method may permit greater portability of a procedure found effective to produce a specific product on one system to a large number of other cell processing systems, while still providing the option of addressing local variations in the nature of the biological fluid being processed. Other advantages may also result.

Having thus described the system and method in general terms, the details of the system and method are described in detail.

As mentioned above, the systems disclosed herein typically include a reusable separation apparatus and one or more disposable processing circuits adapted for association with the reusable apparatus, which apparatus and circuit(s) define the processor. The reusable separation apparatus may be any apparatus that can provide for the automated processing of biological fluid. "Biological fluid" includes without limitation blood and blood components, and "cell" or "biological cell" includes without limitation blood cells, such as red cells, white cells and platelets. By "automated,"

it is meant that the apparatus can be programmed to carry out the processing steps of a biological fluid processing method without substantial operator involvement. Of course, even in the automated system of the present disclosure, it will be understood that operator activity may be involved, including the loading of the disposable fluid circuits and entering processing parameters. Additional manual steps may be required as well. However, the reusable apparatus can process biological fluid through the disposable circuit(s) described below without substantial operator intervention.

Figure 6:
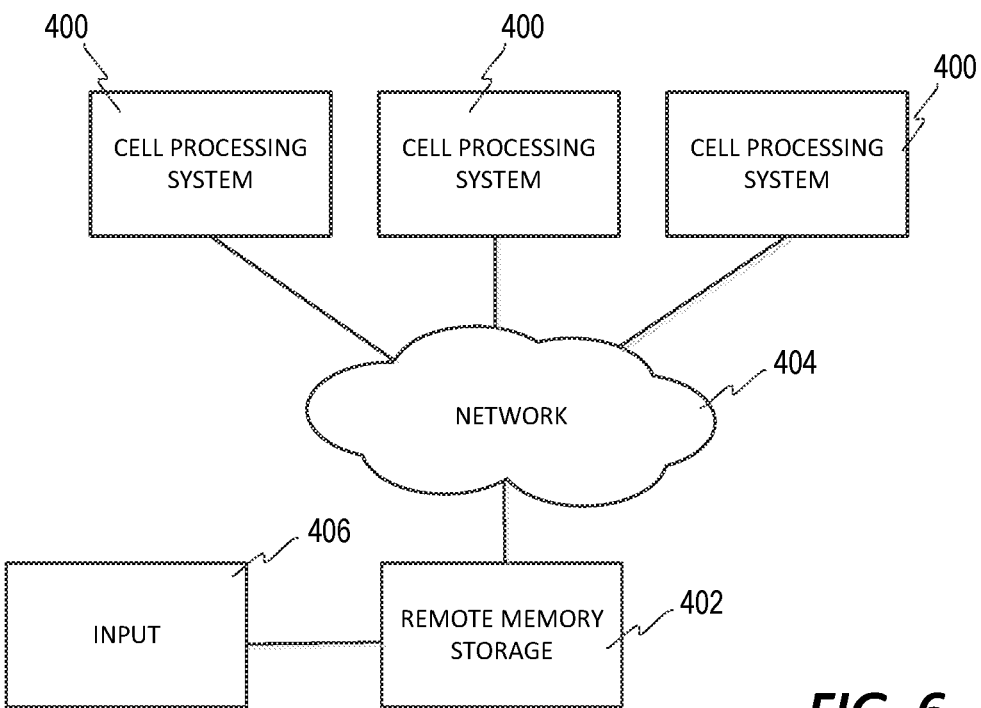
FIG. 6 is a schematic view of a network of cell processing systems and at least one memory storage device.

The illustrated processing apparatus is typically capable of effecting the separation of a biological fluid that includes biological cells into two or more components or fractions. Thus, the reusable apparatus may generate conditions that allow for the separation of a biological fluid into selected components or fractions, One preferred machine for separating biological fluid into its constituent components or fractions uses a spinning porous membrane. An example of such machine is the Autopheresis C® sold by Fenwal, Inc, of Lake Zurich, Ill., A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which is also incorporated herein in its entirety. In addition, systems and methods that utilize a spinning porous membrane are also disclosed in U.S. Provisional Patent Application No. 61/537,856, filed on Sep. 22, 2011, and International (PCT) Application No. PCT/US2012/028522, filed Mar. 9, 2012, the contents of each are incorporated herein by reference. The references identified above describe a membrane covered spinner having an interior collection system disposed within a stationary shell. While a detailed discussion of the separation device is beyond the scope of this application, the spinning membrane separation device is shown in FIGS. 6, 7(a)-7(b) of the reference cited and is discussed below in general terms. In another embodiment, the reusable apparatus may generate a centrifugal field to effect separation.

Figure 3:
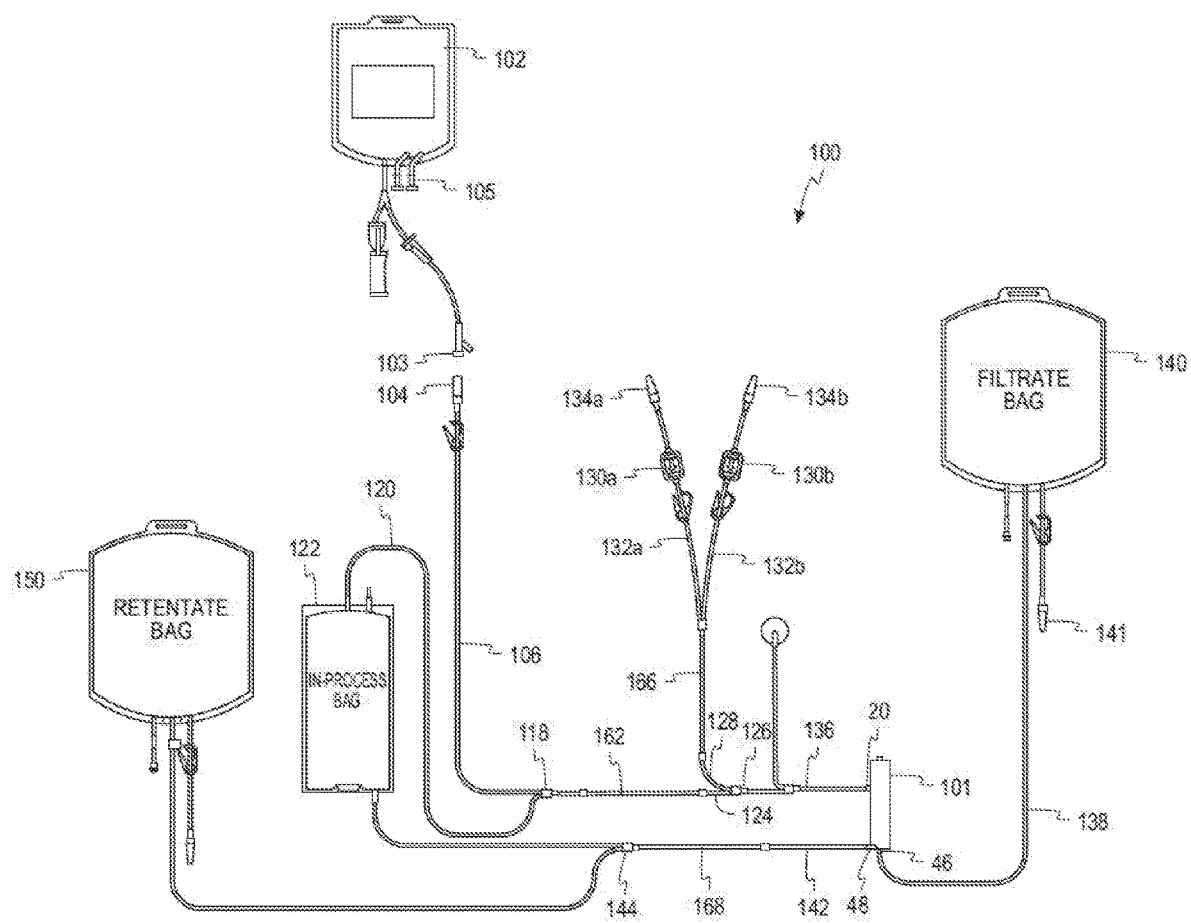
FIG. 3 is a schematic view of one embodiment of a disposable fluid circuit useful in the systems and methods described herein.

Turning now to FIG. 3, the systems described herein include at least one disposable fluid circuit 100 for use in the processing of biological fluid. While the circuits described herein may be used as stand-alone circuits, more preferably, at least two or more disposable fluid circuits are used in combination and in series for the separation; washing, volume reduction and/or other processing of a biological fluid. Circuit 100 may include an integrated separation device, such as, but not limited to, the spinning membrane 101 described above. Circuit 100 may also include waste container 140, product container 150, and in-process container 122. Disposable fluid circuits of the type described below may further include sampling assemblies (not shown) for collecting samples of source biological fluid, "final" product, or other intermediate products obtained during the biological fluid processing.

As will be seen in the Figures and described in detail below, the disposable fluid processing circuits include tubing that defines flow paths throughout the circuits, as well as access sites for sterile or other connection to containers of processing solutions, such as wash solutions, treating agents, or sources of biological fluid. As shown in FIG. 3, the tubing of circuit 100 includes spaced tubing segments identified by reference numerals 162, 166, 168. The tubing segments are provided for mating engagement with the peristaltic pumps 202, 204, 206 of the reusable hardware apparatus 200 discussed below. The containers and the plastic tubing are made of conventional medical grade plastic that can be sterilized by sterilization techniques commonly used in the medical field such as, but not limited to, radiation or autoclaving. Plastic materials useful in the manufacture of containers and of the tubing in the circuits disclosed herein include plasticized polyvinyl chloride. Other useful materials include acrylics. In addition, certain polyolefins may also be used.

As will be apparent from the disclosure herein, source containers may be attached in sterile fashion to the circuit 100. Source containers 102 for connection to one disposable circuit may be the product containers 150 of another circuit used in an earlier step of the overall method of processing. Alternatively, the contents of a product container 150 may be further processed or separated and then transferred in sterile fashion to the source container 102 of a later-in-series fluid circuit.

The biological cell suspension to be washed or otherwise treated is typically provided in a source container 102, shown in FIG. 3 as (initially) not connected to the disposable set. As noted above, source container 102 may be attached (in sterile fashion) at the time of use, Source container 102 has one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source container 102.

As further shown in FIG. 3, tubing segment 106 extends from docking site 104 and is connected to further downstream branched-connector 118. Branched-connector 118 communicates with tubing 106 and tubing 120, which provides a fluid flow path from "in-process" container 122, described in detail below. Tubing segment 124 extends from branched-connector 118 and is joined to a port of further downstream branched-connector 126. A separate flow path defined by tubing 128 is also connected to a port of branched-connector 126.

In accordance with the fluid circuit of FIG. 3, one or more containers of wash or other processing/treating solution may be attached (or pre-attached) to set 100. As shown in FIG. 3, tubings 132a, 132b (defining a flow path) preferably include and terminate in an access site such as spike connectors 134a, 134b. Access sites 134a, 134b are provided to establish flow communication with containers 135a, 135b (shown in FIG. 1) of a wash fluid, such as saline or other solution. Tubings 132a, 132b may include in-line sterile barrier filters 130a, 130b for filtering any particulate from a fluid before it enters the flow path leading to second branched-connector 126 and, ultimately separator 101. In one embodiment, the sterile barrier filters 130a, 130b may be 0.2 μm filters. The wash medium or fluid flows from the wash fluid source through tubing segments 132a, 132b where it is filtered by the sterile barrier filters 130a, 130b described above, and then passes through tubing 128 to the input of the branched-connector 126 described above.

Tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. Nos. 5,194,145 and 5,053,121, which are incorporated by reference, U.S. Provisional Patent Application Ser. No. 61/451,903 and PCT/US2012/028522, also previously incorporated herein by reference.

As shown in FIG. 3 (and described in detail in connection with FIG. 5), the spinning membrane separator 101 has at least two outlet ports. Outlet 46 of separator 101 receives the waste from the wash (i.e., the diluted suspension medium) and is connected to tubing 138, which defines a flow path to waste product container 140. The waste product container includes a further connection port 141 for sampling or withdrawing the waste from within the product container.

Separation device 101 preferably includes a second outlet 48 that is connected to tubing segment 142 for directing the desired biological cell/fluid product to "final" product container. The other end of tubing segment 142 is connected to branched-connector 144, which branches into and defines a flow path to one or more in-process containers 122 and a flow path to a final product container 150. The final product container 150 may also include a sampling assembly (not shown).

Figure 4:
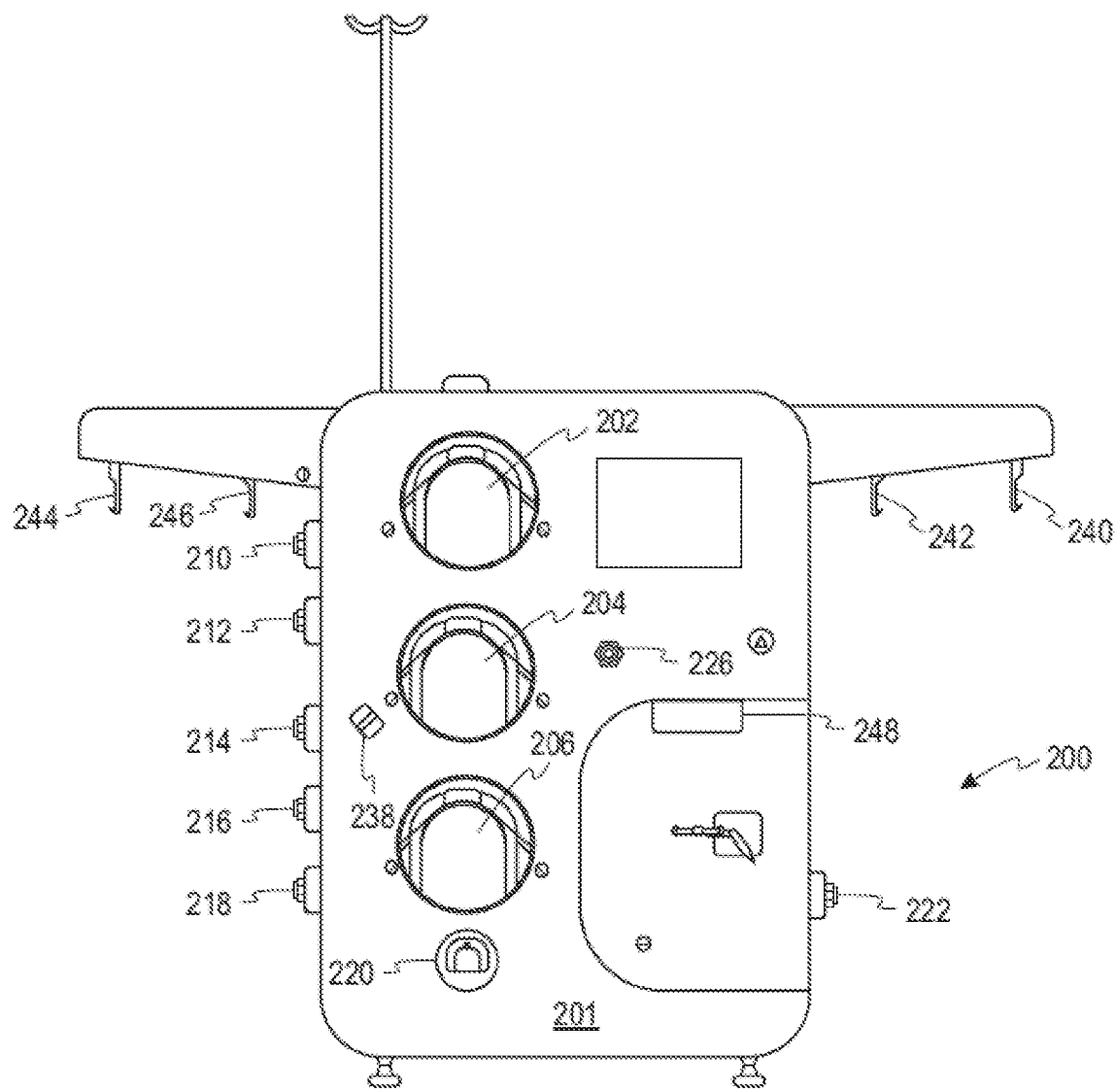
FIG. 4 is a frontal view of the reusable cell processing apparatus.

FIG. 4 shows the front panel 201 of reusable hardware processing apparatus 200, also referred to herein as "hardware". Apparatus 200 may be of compact size suitable for placement on a table top of a lab bench and adapted for easy transport. Alternatively, apparatus 200 may be supported by a pedestal that can be wheeled to its desired location. In any event, as shown in FIG. 4, apparatus 200 includes a plurality of peristaltic pumps such as pumps 202, 204 and 206 on front panel 201. Pump segments of the disposable fluid circuit (described above) are selectively associated with peristaltic pumps 202, 204, and 206. The peristaltic pumps articulate with the fluid set of FIG. 3 at the pump segments identified by reference numerals 162, 166, 168 and advance the cell suspension or other fluid within the disposable set, as will be understood by those of skill in the art. Apparatus 200 also includes clamps 210, 212, 214, 216, 218, 220 and 222. The clamps are used to control the flow of the cell suspension through different segments of the disposable set, as described above.

Apparatus 200 also includes several sensors to measure various conditions. The output of the sensors is utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at; for example, tubing segment 136), to monitor pressure inside separator 101. Air detector sensor 238 may also be associated with the disposable set 100, as necessary. Air detector 238 is optional and may be provided to detect the location of fluid/air interfaces.

Apparatus 200 includes weight scales 240, 242, 244, and 246 from which the final product container, in-process container, source container, and any additional container(s), respectively, may depend and be weighed. The weights of the bags are monitored by weight sensors and recorded during a washing or other procedure, From measurements of the weight sensors, the device determines whether each container is empty, partially full, or full and controls the components of apparatus 200, such as the peristaltic pumps 202, 204 and 206 and clamps 210, 212, 214, 216, 218, 220 and 222.

Apparatus 200 includes at least one drive unit or "spinner" 248, which causes the indirect driving of the spinning membrane separator 101. Spinner 248 may consist of a drive motor connected and operated by apparatus 200, coupled to turn an annular agnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 5:
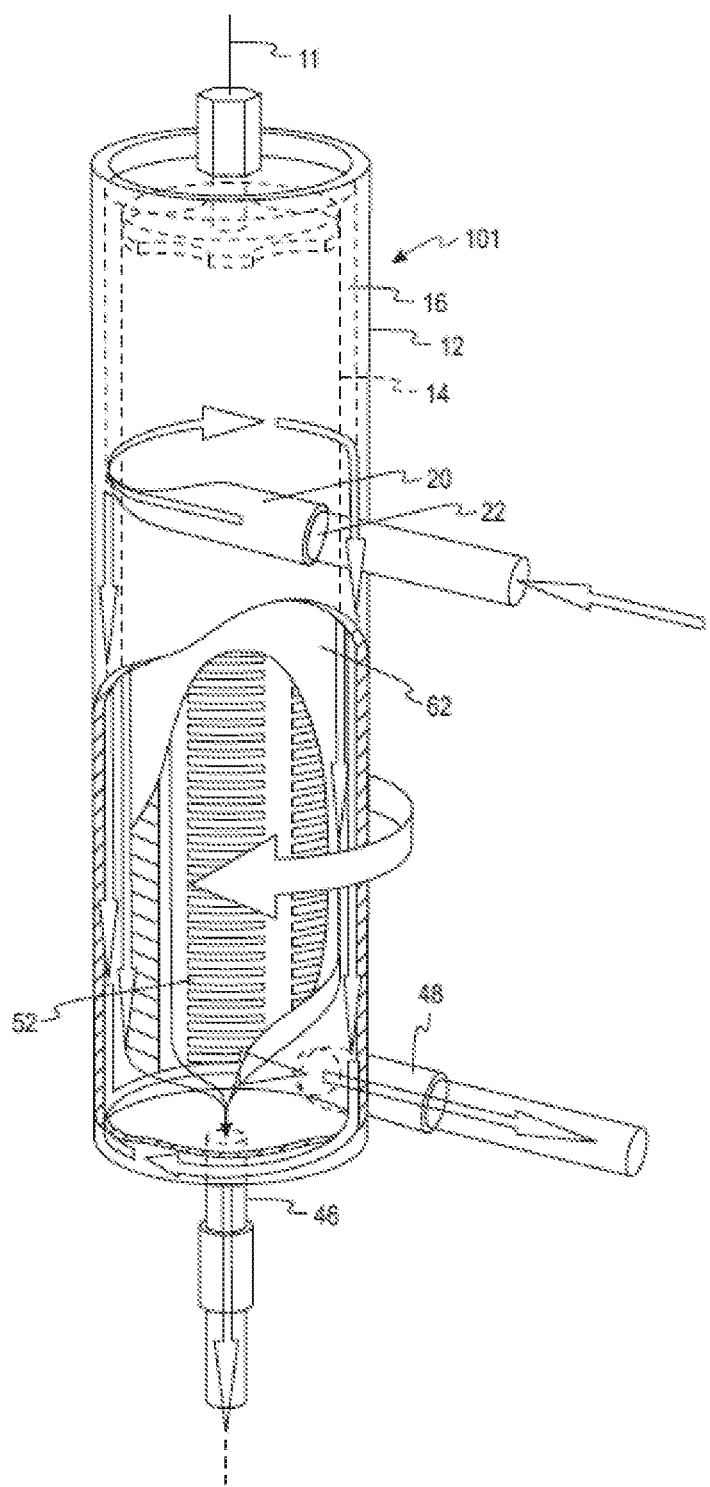
FIG. 5 is a perspective view of a separation/washing device using a spinning membrane.

Turning to FIG. 5, a spinning membrane separation device, generally designated 101, is shown. Such a device 101 forms part of the disposable circuit 100.

Device 101 includes a generally cylindrical housing 12, mounted concentrically about a longitudinal vertical central axis, An internal member 14 is mounted concentric with the central axis 11. Housing 12 and internal member 14 are relatively rotatable. In the preferred embodiment, as illustrated, housing 12 is stationary and internal member 14 is a rotating spinner that is rotatable concentrically within cylindrical housing 12, as shown by the thick arrow in FIG. 5. The boundaries of the flow path are generally defined by gap 16 between the interior surface of housing 12 and the exterior surface of rotary spinner 14. The spacing between the housing and the spinner is sometimes referred to as the shear gap. In one non-limiting example, the shear gap may be approximately 0.025-0.050 inches (0.067-0.127 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.025 to about 0.075 inches (0.06-0.19 cm), The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48.

Cylindrical housing 12 is completed by a bottom end housing terminating in an outlet orifice 46 concentric with the central axis.

In the illustrated embodiment, the surface of the rotary spinner 14 is at least partially, and is preferably substantially or entirely, covered by a cylindrical porous membrane 62. The membrane 62 typically has a nominal pore size of 4.0 microns, but other pore sizes, for example, of from 0.8 microns to 30.0 microns, may alternatively be used. Membranes may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In an embodiment, the nylon membrane may have a pore size of approximately 4.0 μm and a thickness of approximately 10 μm or greater. Membranes of this type will typically retain all cellular components (e.g., red blood cells, white blood cells) and certain formed blood components, e.g., platelets. In another embodiment, the membrane may be made of a thin (approximately 10-50 micron (μm) thick) sheet of, for example, polycarbonate. In this embodiment, pores (holes) may be cylindrical and larger than those described above. The pores may be sized to allow small formed components (e.g., platelets, microparticles, etc.) to pass, while the desired cells (e.g., white blood cells and larger red blood cells) are collected.

Having thus described the processor, including disposable circuit 100 and reusable hardware 200, reference is made to FIG. 2 to discuss additional details of the control unit or controller 300. As mentioned above, the controller 300 may include a microprocessor 304 (which, in fact may include multiple physical and/or virtual processors). According to other embodiments, the controller 300 may include one or more electrical circuits designed to carry out the actions described herein. In fact, the controller 300 may include a microprocessor and other circuits or circuitry. In addition, the controller 300 may include one or more memories 306, The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304, may cause the microprocessors 304 to carry out one or more actions as described below.

As is also illustrated in FIG. 2, the controller 300 may be coupled to one or more of the structures described above, for example to receive information (e.g., in the form of signals) from these structures or to provide commands (e.g., in the form of signals) to these structures to control the operation of the structures. As illustrated, the controller 300 may be coupled to the scales 240, 242, 244, 246, the sensors 226, 238 and the at least one input 302 to receive information from those devices. Additionally, the controller 300 may be coupled to the pumps 202, 204, 206, the clamps 210, 212, 214, 216, 218, 220, 222, and the drive 248 to provide commands to those devices to control their operation. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel 201 of the device 200, the video display 308 also being coupled to the controller 300. The input could also include a reader or scanner, such as a barcode reader or scanner or an RFID reader. The assembly of the input/touch screen 302 and video display 308 may be one of the afore-mentioned structures to which the controller 300 is coupled from which the controller 300 receives information and to which the controller 300 provides commands. According to still other embodiments, the input 302 may be in the form of computer equipment that permits the cell processing system including the controller 300 to communicate (whether via wires or wirelessly) with other cell processing systems over a local network, or with other cell processing systems or other computer equipment (e.g., a server) over local networks, wide area networks, or the Internet. According to such an embodiment, the input may include an internal transmitter/receiver device.

Having discussed the structure of embodiments of the cell processing system disclosed herein, the operation of the cell processing system is now discussed. In this regard, reference is made to U.S. Patent Application Pub. No. US 2013/0092630, the contents of which are incorporated herein by reference, which document discloses methods and systems for washing biological cells using a reusable hardware apparatus and disposable fluid circuit including a spinning membrane separator which may be generally applicable to the cell processing system described herein. The methods disclosed in this document involve the processing, washing, treating and incubating of biological cells, such as mononuclear cells for subsequent therapeutic administration.

In general terms, the apparatus 200 first may be activated (e.g., switched on), at which point the apparatus 200 conducts self-calibration checks, including the checking of the peristaltic pumps 202, 204, 206, clamps 210, 212, 214, 216, 218, 220, 222, and sensors 226, 238. Apparatus 200 may then prompt the user to enter or modify process parameters, such as may be used in a washing procedure, including the amount of cell suspension to be washed, the number of washings to take place, etc. The user's ability to enter or modify process parameters may depend on (i) the authorization associated with the user, which authorization may be determined by the controller 300 according to an identifier that is received by the controller 300 via the input 302, and/or (ii) one or more process parameter controls that may be associated with a specific process parameter at the time the apparatus 200 is activated or thereafter.

As to authorizations, the user may use the input 302 to provide an identifier, which is in turn received by the controller 300 coupled to the input 302. The controller 300 may be configured (in the case of a microprocessor, may be programmed) to determine if the identifier received from the input 302 is associated with an authorization that permits the user (i) to enter and/or modify the process parameters (and/or to enter and/or modify process parameters within a controlled range) and/or (ii) enter and/or modify process parameter controls. This determination may be made any time a user attempts to enter or modify process parameters, or the determination may be made only when a user attempts to enter or modify a process parameter control, according to certain embodiments.

By way of a non-limiting example, a hierarchy of authorizations may exist with at least two different levels of authorization: an administrator authorization and an operator authorization. If the controller 300 determines that the identifier received from input 302 is associated with an administrator authorization, then the user may be permitted to enter or modify process parameter controls and/or to enter or modify process parameters without limitation (which may or may not result in a modification of the process parameter controls already in existence). In fact, the modification of a process parameter control (or unrestricted ability to modify a process parameter) may include removal of a process parameter control. On the other hand, if the controller 300 determines that the received identifier is associated with an operator authorization, the user may only enter or modify the process parameters to the extent permitted by any process parameter controls that may exist relative to the process parameter in question, and the user may not enter or modify the process parameter controls. According to one embodiment, the controller 300 may assume as a default that the user has only operator authorization unless the user attempts to enter an identifier, at which point the controller 300 determines if the user has administrator authorization depending on the identifier received via the input 302.

The identifier may take various forms, and the method by which the controller 300 determines of the authorization associated with the identifier may include various actions.

As one example, the identifier may be an alphanumeric password or passcode, which may be entered using an input 302 in the form of a keyboard, keypad, or touchscreen. The controller 300 may compare the password or passcode to a list of passwords or passcodes associated with persons having administrator authorization, which list may be stored in the memory 306 or may be stored remotely relative to the cell processing system (e.g., accessible by the controller 300 over a network). If the password or passcode matches one of the passwords or passcodes in the list, the controller determines that the identifier is associated with an administrator authorization, and determines if additional commands (such as at least one process parameter control) have been received from the user and applies those commands. On the other hand, if the password or passcode does not match one of the passwords or passcodes in the list, the controller determines that the identifier is not associated with an administrator authorization (and optionally that the identifier is associated with another level of authorization), and ignores any additional commands received from the user.

It will be recognized that the use of an alphanumeric password or passcode is only one possible embodiment. According to other embodiments, the identifier may be a two-dimensional or three-dimensional barcode printed on a badge or key that is read by an input 302 in the form of a barcode reader. As another embodiment, the identifier may be stored on a memory storage device, such as may be carried on a badge or card, the input 302 being in the form of a reader than can form an electrical and/or magnetic communication link with the memory storage device to read the identifier stored thereon. Other possible embodiments also exist.

The nature of the process parameter controls that may be entered or modified if the controller 300 determines that the user has a sufficient level of authorization (e.g., administrator authorization) are numerous. As one example, consider a process parameter in the form of a rinse flow rate that is used by the controller 300 in controlling the processor 100, 200 according to the method of operation of the cell processing system, additional details of which are provided below. According to an embodiment, the rinse flow rate process parameter may be a numeric value the controller 300 uses to vary the operation of the pumps 202, 204, 206, for example. In general, the numeric value associated with the rinse flow rate process parameter may have an initial (or default) value, which may be modified to a second value. However, it may be desirable to place controls on the rinse flow rate process parameter, for example, to ensure that the default value is in keeping with a previously determined value (e.g., which may exist from a single previous procedure run on the system, or may be an empirically-determined value for use according to a particular protocol), and to ensure that the process parameter either is no longer modifiable (i.e., locked) or that the process parameter is modifiable only within a range of values (having a minimum and/or a maximum).

According to such an embodiment, a user having an identifier associated with administrator authorization may provide the identifier to the controller 300 along with a process parameter control in the form of, for example:
 a default value (e.g., 100 mL/min);
 an operator editable setting (e.g., modifiable or non-modifiable/locked);
 a minimum (e.g., 20 mL/min); or
 a maximum (e.g., 100 mL/min).
Assuming that the administrator does not lock the process parameter, and instead enters a default value and the minimum and maximum listed above, a non-administrator user (e.g., an operator) could run a procedure on the system using the default value of 100 mL/min, or could modify the process parameter to another value within the controlled range from 20 mL/min to 100 mL/min before running the procedure. The non-administrator user/operator could not, however, run a procedure using a rinse flow rate below 20 mL/min or above 100 mL/min. Stated more generally, the process control parameter would prevent modification of the at least one process parameter outside of the range without an identifier associated with an administrator authorization.

More than one process parameter control may exist at one time relative to an embodiment of the present cell processing system. A user having administrator authorization may create a protocol that includes a plurality of process parameter controls, and the controller 300 may apply the process parameter controls of the protocol if an identifier associated with an administrator authorization is also received. Further, the process parameter controls that are included in the protocol need not be identical: the controls associated with certain process parameters may prevent modification by a non-administrator user or operator, while other controls may permit modification by an operator relative to a default value within a range of values, which range may or may not have a defined minimum or maximum. Moreover, the administrator may create such a protocol including a plurality of process parameter controls to preserve (i.e., lock) even process parameter settings entered by a non-administrator user. An administrator may enter each process parameter control in the controller 300 via input 302 in the form of a keyboard, keypad, touchscreen, etc., or alternatively, the administrator may transmit, transfer, or otherwise store in the memory 308 of the controller 300 a protocol including a plurality of process parameter controls from another memory storage device, such as may be associated with a portable memory storage device or a remote memory storage device (e.g., server).

As to this latter case, FIG. 6 illustrates a network of cell processing systems 400 coupled to a non-transitory computer-readable memory storage device 402 via a network 404. The network 404 may be a local network, a wide area network, or the Internet, for example, and may be implemented via wires/cables or wirelessly.

According to certain embodiments, at least one of (and sometimes all of) the cell processing systems 400 may include the details of the above-mentioned system. That is, the at least one cell processing system 400 may include a processor to receive a biological fluid to be processed, a control unit or controller coupled to the processor, the controller configured to operate the processor according to at least one modifiable process parameter, at least one input coupled to the controller, the at least one input configured to receive an identifier and at least one process parameter control associated with the at least one process parameter that limits modification of the at least one process parameter if applied. The controller may be configured to determine if the identifier is associated with an administrator authorization and to apply the at least one processor parameter control to the at least one process parameter if the identifier is associated with an administrator authorization.

According to other embodiments, the cell processing systems 400 may include a processor to receive a biological fluid to be processed, a controller coupled to the processor, the controller configured to operate the processor according to at least one modifiable process parameter, and at least one input coupled to the controller, the at least one input configured to receive at least one process parameter control associated with the at least one process parameter that limits modification of the at least one process parameter if applied. The controller is also configured to apply the at least one processor parameter control to the at least one process parameter if an identifier associated with an administrator authorization is received.

The memory storage device 402, which may include one or more tangible non-transitory computer-readable memories, has computer executable instructions stored thereon, which when executed by the cell processing systems 400 (or more particularly, the controllers of the cell processing systems 400), may cause the cell processing systems 400 to apply at least one process parameter control to one or more process parameters if an identifier associated with an administrator authorization is received as well, According to one embodiment, the memory storage device 402 has stored thereon a plurality of process parameter controls, which controls may be in the form of one or more protocols according to certain embodiments. The memory storage device 404 may also be configured to transmit one or more process parameter controls to one or more cell processing systems 400.

According to such a network of systems 400, one of (i) the controller of the system 400 and (ii) the memory storage device 402 is configured to receive an identifier and to determine if the identifier is associated with an administrator authorization. For example, the input 302 may be configured to receive an identifier and the controller 300 may be configured to determine if the identifier is associated with an administrator authorization. However, according to a preferred embodiment, the memory storage device 402 may instead be associated with an input 406, which input 406 is configured to receive an identifier and may be similar in structure and operation to the input 302 as described above, and the memory storage device 402 may be configured to determine if the identifier is associated with an administrator authorization. Such an embodiment limits the need to provide and maintain a list or database of administrator authorizations at each of the systems 400, although such an embodiment does not exclude the possibility that the systems 400 include such a list or database. In either event, an administrator (i.e., a user associated with administrator authorization) may use the input to provide their identifier and to control the memory storage device 404 to download to one of the systems 400 (via the input 302, for example) one or more process parameter controls stored on the memory storage device 404. As a further alternative, the administrator may control the memory storage device 404 to download their identifier and the one or more process parameter controls to one or more of the systems 400, whereupon the system 400 may make the determination as relates to the identifier and apply the one or more process parameter controls accordingly.

After the user has entered and/or modified the process parameters (to the extent permitted by existing process parameter controls), the apparatus 200 may then confirm the parameter entry and prompt the operator to load the disposable set. The operator then loads the disposable set onto the panel 201 of apparatus 200. In one exemplary embodiment, the disposable set may be the fluid circuit 100 of FIG. 3. After installation of the disposable set, apparatus 200 confirms installation.

After the disposable set is mounted, apparatus 200 automatically checks to determine whether the disposable set is properly installed. After apparatus 200 determines that the disposable set is properly installed, the controller prompts the operator to connect the biological fluid (e.g., 102 of FIG. 3) and wash medium (e.g., 135a, 135b of FIG. 3). The operator then connects the wash medium (such as, but not limited to saline) to the disposable set via a spike connector (e.g., 134a, 134b of FIG. 3). The operator then connects source container of the biological fluid or biological cell product (typically derived from an earlier, separate procedure) to the disposable set via a spike connector or sterile connection (e.g., 103, 104 of FIG. 3) as previously described. In one embodiment, the source of biological fluid/cells may be apheresis-collected mononuclear cells.

After the source of biological fluid and wash medium are connected to the disposable set, the operator confirms that the solutions are connected. The device prompts the operator to take a cell suspension sample. The operator or the device then opens sampling assembly clamp to introduce fluid into the sample chamber of the sampling assembly. Once the sample chamber is sufficiently filled, it is then sealed and removed from the disposable circuit. The operator confirms that a sample has been taken. Following the removal of the sample chamber, the disposable fluid circuit is primed for the wash process. In one embodiment, the circuit may be primed with saline, although other bio-compatible aqueous solutions may also be used.

The controller of separation apparatus then commences the wash process. The biological cells to be washed are transferred from source container (e.g., 102 of FIG. 3) through the disposable set to the spinning membrane separator 101 via the operation of one or more peristaltic pumps 202, 204 and 206. Likewise, the wash medium is delivered from its container, through the disposable circuit to the spinning membrane separator 101. In a preferred embodiment, the original cells of the cell suspension are concentrated and/or collected in either an in-process bag (e.g., 122 of FIG. 3) for further processing or collected in a final product container (e.g., 150 of FIG. 3), while supernatant is separated and removed to waste container (e.g., 140 of FIG. 3), In a preferred embodiment, the process provides a final concentrated biological cell product resuspended in approximately 200 mL of the wash (e.g., saline) solution with approximately a 2 log reduction of supernatant contents. If further washing or diluting of the cell suspension is necessary, the cell suspension in the in-process bag may be washed (a second time) with the same or different wash medium following the process outlined above. Prior to the conclusion of each wash cycle, the cell suspension volume or weight is measured and recorded. When the concentration of the cells to wash medium reaches an acceptable level, the final product bag is filled. Once the desired volume of the final product is collected, the control and operation device prompts the operator to sample and seal the final product container. After sampling, the operator then seals and removes from the disposable circuit the washed cell suspension in the final product container 150.

The systems and methods described herein may also be effective in the washing of cells such as red blood cells and/or white blood cells. In one example of red cell washing, stored red blood cells may be washed to remove accumulated free hemoglobin, spent storage solution, or other desirable extracellular components. The solution may be sterile docked or otherwise included in the closed system of the disposable processing sets of the type described above. The treated cells may then be washed with a washing solution such as saline, Adsol or E-Sol (the latter of which are red blood cell storage solutions and generally comprise dextrose, mannitol and a buffer) to reconstitute the red blood cells for subsequent storage and transfusion.

The initial cell feed may be diluted by combining the feed from container 102 with diluent (wash solution) from container 135 at branched connector 126. In one embodiment, diluent from container 135 may initially be drawn into separator, followed by the cell feed drawn from container 102 and combined with the diluent, as described.

Thus, an improved method and system have been disclosed for the processing of biological cells. The description provided above is intended for illustrative purposes only and is not intended to limit the scope of the invention to any specific method, system, or apparatus, or device described herein except as may be explicitly delineated above.

In conclusion, according to one aspect, a cell processing system includes a processor to receive a biological fluid to be processed, a controller coupled to the processor, the controller configured to operate the processor according to at least one modifiable process parameter, and at least one input coupled to the controller, the at least one input configured to receive an identifier and at least one process parameter control associated with the at least one process parameter that limits modification of the at least one process parameter if applied. The controller is configured to determine if the identifier is associated with an administrator authorization and to apply the at least one processor parameter control to the at least one process parameter if the identifier is associated with an administrator authorization In such a system, the identifier may be a password. In addition, the at least one modifiable process parameter may be a numeric value, and the at least one process parameter control comprises at least one of a minimum value and a maximum value. Further, the at least one process parameter control may prevent modification of the at least one process parameter without an identifier associated with an administrator authorization.

The controller may be configured to receive a protocol comprising a plurality of process parameter controls, and the controller may apply the process parameter controls of the protocol if the identifier is associated with an administrator authorization. Indeed, the at least one input may receive the protocol from another cell processing system in communication with the cell processing system.

In addition, the controller may be a microprocessor, and the microprocessor may be programmed to determine if the identifier is associated with an administrator authorization and to apply the processor parameter control to the at least one process parameter if the identifier is associated with an administrator authorization.

According to any of the foregoing, the processor may include a disposable fluid circuit and reusable hardware. The disposable fluid circuit may include a spinning membrane separation device, at least one container, and tubing connecting the spinning membrane and the one or more containers. The reusable hardware may include at least one drive to spin the spinning membrane, at least one scale to weigh the at least container and contents thereof, and at least one pump.

According to another aspect, a method of operating a cell processing system, the cell processing system comprising a processor to receive a biological fluid to be processed and to be operated according to at least one modifiable process parameter. The method includes receiving an identifier and at least one process parameter control associated with the at least one process parameter that limits modification of the at least one process parameter if applied, determining if the identifier is associated with an administrator authorization, applying the at least one processor control to the at least one process parameter if the identifier is associated with an administrator authorization, and processing the biological fluid employing a process that includes the at least one process parameter.

According to such a method, receiving an identifier may include receiving a password. The at least one modifiable process parameter may be a numeric value, and applying the at least one process parameter control may include applying at least one of a minimum value and a maximum value. In addition or in the alternative, the at least one process parameter control may include preventing modification of the at least one process parameter without an identifier associated with an administrator authorization.

According to other aspects of the method, receiving at least one process parameter control includes receiving a protocol comprising a plurality of process parameter controls, and applying at least one process parameter control includes applying the process parameter controls of the protocol if the identifier is associated with an administrator authorization. Receiving the protocol may include receiving the protocol from another cell processing system in communication with the cell processing system.

According to still another aspect, a network of cell processing systems includes at least one cell processing system and a non-transitory computer-readable memory storage device. The at least one cell processing system includes a processor to receive a biological fluid to be processed, a controller coupled to the processor, the controller configured to operate the processor according to at least one modifiable process parameter, and at least one input coupled to the controller, the at least one input configured to receive at least one process parameter control associated with the at least one process parameter that limits modification of the at least one process parameter if applied. The non-transitory computer-readable memory storage device is coupled to the at least one cell processing system, includes a plurality of process parameter controls stored therein and is configured to transmit one or more process parameter controls to the at least one cell processing system. One of the controller and the memory storage device is configured to receive an identifier and to determine if the identifier is associated with an administrator authorization. The controller is also configured to apply the at least one processor parameter control to the at least one process parameter if the identifier is associated with an administrator authorization.

In such a network, one or more protocols are stored in the memory storage device, each protocol comprising a plurality of process parameter controls. The one or more protocols may be transmitted from one or more of the cell processing systems to the memory storage device. The one or more identifiers also may be stored in the memory storage device, and the one or more identifiers may be transmitted from the memory storage device to the at least one cell processing system.

The invention claimed is:

1. A cell washing system, comprising:
   a fluid circuit;
   a source container configured to hold a biological cell suspension, the source container comprising an access site configured to provide access between the source container and the fluid circuit;
   a source of wash solution configured to hold a wash solution, the source of wash solution comprising an access site configured to provide access between the source of wash solution and the fluid circuit, wherein the fluid circuit is configured to combine the biological cell suspension and the wash solution;

a pump configured to pump the combination of biological cell suspension and wash solution through the fluid circuit;

a separator device comprising a drive unit and a port, the port configured to receive the combination of biological cell suspension and wash solution, wherein the separator device is configured to separate red blood cells from a waste solution comprising free hemoglobin, the separator device to dispense the waste solution to a waste product container;

a touch screen configured to receive user input data and to display data to a user; and a controller coupled to the touch screen and configured to control the separator device and pump to operate a wash procedure, wherein the controller is configured to receive from the touch screen user input data for a plurality of protocols, each protocol comprising values for a set of process parameters for wash procedures, wherein the user input data from the touch screen comprises a numeric value for a washing procedure parameter, wherein the controller is configured to store the numeric value of the washing procedure parameter as part of one of the prestored protocols in a memory, wherein the controller is configured to receive an identifier from a user via the touch screen, to determine if the identifier permits the user to modify the one of the prestored protocols, and to receive a modification of the one of the prestored protocols from the user via the touch screen if permitted, wherein the modification comprises a modification of the numeric value of the washing procedure parameter, wherein the controller is configured to apply the one of the prestored protocols with the modification of the numeric value of the washing procedure parameter and to operate the wash procedure using the applied protocol, wherein the controller is configured to provide a hierarchy of authorizations comprising at least an administrator authorization and an operator authorization, the operator authorization having a lower level of authorization than the administrator authorization, wherein the controller is configured to receive an identifier from the touchscreen, to compare the identifier to a list of passwords stored in memory and, if the identifier matches one of the passwords in the list, the controller determines that the identifier is associated with an administrator authorization, wherein if additional commands are then received from the user, the controller applies those received commands based on the match, wherein the controller is configured to assume as a default that the user has operator authorization unless the user attempts to enter the identifier, at which point the controller determines if the user has an administrator authorization, the administrator authorization being the authorization that permits the user to apply the received commands.

2. The cell washing system of claim 1, wherein the values for the set of process parameters are default values.

3. The cell washing system of claim 1, wherein the controller is configured to determine whether the disposable set is properly installed and, if so, to confirm installation of the disposable set.

4. The cell washing system of claim 3, wherein the controller is configured to communicate with a remote server over a network.

5. The cell washing system of claim 2, wherein the default values are modifiable by a user.

6. The cell washing system of claim 1, wherein at least one of the process parameters is a process parameter control for limiting modification of the parameter by a non-authorized user.

7. The cell washing system of claim 1, wherein the applied protocol is received from a portable memory storage device or a server.

8. A cell washing system, comprising:

a fluid circuit;

a source container configured to hold a biological cell suspension, the source container comprising an access site configured to provide access between the source container and the fluid circuit;

a source of wash solution configured to hold a wash solution, the source of wash solution comprising an access site configured to provide access between the source of wash solution and the fluid circuit, wherein the fluid circuit is configured to combine the biological cell suspension and the wash solution;

a pump configured to pump the combination of biological cell suspension and wash solution through the fluid circuit;

a separator device comprising a drive unit and a port, the port configured to receive the combination of biological cell suspension and wash solution, wherein the separator device is configured to separate red blood cells from a waste solution comprising free hemoglobin, the separator device to dispense the waste solution to a waste product container;

a touch screen configured to receive user input data and to display data to a user; and a controller coupled to the touch screen and configured to control the separator device and pump to operate a wash procedure, wherein the controller is configured to receive from the touch screen user input data for a protocol, the protocol comprising values for a set of process parameters for the wash procedure, wherein the user input data received from the touch screen comprises a numeric value for a washing procedure parameter between a minimum value and a maximum value for one of the process parameters of the protocol, wherein the controller is configured to store the protocol having the numeric value of the washing procedure parameter in a memory, wherein the controller is configured to receive an identifier from a user via the touch screen, to determine if the identifier is associated with an authorization that permits the user to modify the protocol, and to receive a modification of the protocol from the user via the touch screen, wherein the modification comprises a modification of the numeric value of the washing procedure parameter, and to process the biological cell suspension employing the wash procedure having the numeric value, wherein the controller is further configured to provide a hierarchy of authorizations comprising at least an administrator authorization and an operator authorization, the operator authorization having a lower level of authorization than the administrator authorization, wherein the administrator authorization permits the user to modify settings, wherein the controller is configured to assume as a default that the user has operator authorization unless the user attempts to enter a password, at which point the controller determines if the user has an administrator authorization, the administrator authorization being the authorization that permits the user to modify the settings.

9. The cell washing system of claim 8, wherein the minimum value and maximum value are user-defined.

10. The cell washing system of claim 9, wherein the values for the set of process parameters are default values.

11. The cell washing system of claim 10, wherein the protocol comprises a process parameter defining a volume to wash.

12. The cell washing system of claim 11, wherein the protocol comprises a process parameter defining a number of washings to take place.

13. The cell washing system of claim 12, wherein the protocol comprises a rinse flow rate.

14. The cell washing system of claim 13, wherein the controller is configured to confirm the protocol applied and to prompt the operator to load a disposable set.

15. The cell washing system of claim 8, wherein the controller is configured to prevent modification of the numeric value without authorization provided by a password.

16. A cell washing system, comprising:
a fluid circuit;
a source container configured to hold a biological fluid comprising red blood cells, the source container configured to couple to the fluid circuit;
a source of wash solution configured to hold a wash solution, the source of wash solution configured to couple to the fluid circuit, wherein the fluid circuit is configured to combine the biological fluid and the wash solution;
a pump configured to pump the combination of biological fluid and wash solution through the fluid circuit;
a separator device comprising a drive unit and a port, the port configured to receive the combination of biological fluid and wash solution, wherein the separator device is configured to separate the red blood cells from a waste solution comprising free hemoglobin, the separator device to dispense the waste solution to a waste product container;
a touch screen configured to receive user input and to display data to a user; and
a controller coupled to the touch screen and configured to control the separator device and pump to operate a wash procedure, wherein the controller is configured to receive from the touch screen user input data for a protocol, the protocol comprising values for a set of process parameters for the wash procedure, wherein the user input data received from the touch screen comprises a numeric value for a washing procedure parameter for one of the process parameters, wherein the controller is configured to store the protocol having the numeric value of the washing procedure parameter in a memory, wherein the controller is configured to receive a password from a user via the touch screen, to determine if the password is associated with an authorization that permits the user to modify the protocol, and to receive a modification of the protocol from the user via the touch screen based on the determination, wherein the modification comprises a modification of the numeric value of the washing procedure parameter, and to process the biological fluid employing a wash procedure having the modified protocol, wherein the controller is configured to provide a hierarchy of authorizations comprising at least an administrator authorization and an operator authorization, the operator authorization having a lower level of authorization than the administrator authorization, wherein the controller is configured to receive an identifier from the touchscreen, to compare the identifier to a list of passwords stored in memory and, if the identifier matches one of the passwords in the list, the controller determines that the identifier is associated with an administrator authorization, wherein if additional commands are then received from the user, the controller applies those received commands based on the match, wherein the controller is configured to assume as a default that the user has operator authorization unless the user attempts to enter a password, at which point the controller determines if the user has an administrator authorization, the administrator authorization being the authorization that permits the user to modify the commands.

17. The cell washing system of claim 16, wherein the controller is configured to confirm the protocol modification and to prompt the operator to load a disposable set.

18. The cell washing system of claim 17, wherein the controller is configured to determine whether the disposable set is properly installed and, if so, to confirm installation of the disposable set.

19. The cell washing system of claim 16, wherein the controller is configured to lock process parameter settings entered by a non-administrator user.

* * * * *